: US 9,968,798 B2
(45) Date of Patent: May 15, 2018

(54) TRANSCRANIAL MAGNETIC STIMULATION DEVICE WITH BODY PROXIMITY SENSORS FOR THE TREATMENT OF MIGRAINE HEADACHES

(71) Applicant: Eneura, Inc., Sunnyvale, CA (US)

(72) Inventors: David R. Fischell, Fair Haven, NJ (US); Robert E. Fischell, Dayton, MD (US); Victor Fei, Vancouver (CA); Priyanka Venkatesh, Ithaca, NY (US); Qi Rui, Anhui Province (CN); Rachel Hyder, Knoxville, TN (US); Abirvab Deb, Acton, MA (US)

(73) Assignee: Eneura, Inc., Sunnyvale, CA (US)

( * ) Notice: Subject to any disclaimer, the term of this patent is extended or adjusted under 35 U.S.C. 154(b) by 466 days.

(21) Appl. No.: 14/315,994

(22) Filed: Jun. 26, 2014

(65) Prior Publication Data

US 2015/0190648 A1 Jul. 9, 2015

Related U.S. Application Data

(63) Continuation-in-part of application No. 14/147,673, filed on Jan. 6, 2014.

(51) Int. Cl.
*A61N 2/02* (2006.01)
*A61N 2/00* (2006.01)

(52) U.S. Cl.
CPC .............. *A61N 2/02* (2013.01); *A61N 2/006* (2013.01)

(58) Field of Classification Search
CPC .................................. A61N 2/006; A61N 2/02
See application file for complete search history.

(56) References Cited

U.S. PATENT DOCUMENTS

| 5,116,304 A | 5/1992 | Cadwell | |
|---|---|---|---|
| 6,402,678 B1 | 6/2002 | Fischell et al. | |
| 8,844,537 B1* | 9/2014 | Abramson | A61N 2/004 128/848 |
| 2001/0018547 A1* | 8/2001 | Mechlenburg | A61N 2/006 600/15 |
| 2001/0039415 A1* | 11/2001 | Francischelli | A61B 18/1402 606/27 |
| 2008/0139872 A1* | 6/2008 | Pasula | A61N 2/02 600/13 |

OTHER PUBLICATIONS

Barker, A.T., et al.; "Non-invasive magnetic stimulation of human motor cortex"; The Lancet, vol. 325, Issue 8437, pp. 1106-1107, May 11, 1985.
Pelka, R.B, et al.; "Impulse magnetic-field therapy for migraine and other headaches: A double-blind, placebo-controlled study"; Medicine Advances in Therapy; vol. 18, No. 3, 101-109; May/Jun. 2001.
Boroojerdi, B., et al.; "Reduction of human visual cortex excitability using 1-Hz transcranial magnetic stimulation"; Neurology; vol. 54 No. 7; pp. 1529-1531; Apr. 11, 2000.

* cited by examiner

*Primary Examiner* — Christine H Matthews
(74) *Attorney, Agent, or Firm* — Rosenberg, Klein & Lee

(57) ABSTRACT

A transcranial magnetic stimulation device has a capacitor for storing electrical energy. A wire coil delivers a magnetic pulse when the capacitor is actuated to cause current flow through the wire coil. A charging circuit charges the capacitor and there is a sensor which includes an unactivated state and an activated state. A control circuit connected to the body sensor initiates the delivery of a magnetic pulse when current from the capacitor flows through the wire coil.

30 Claims, 10 Drawing Sheets

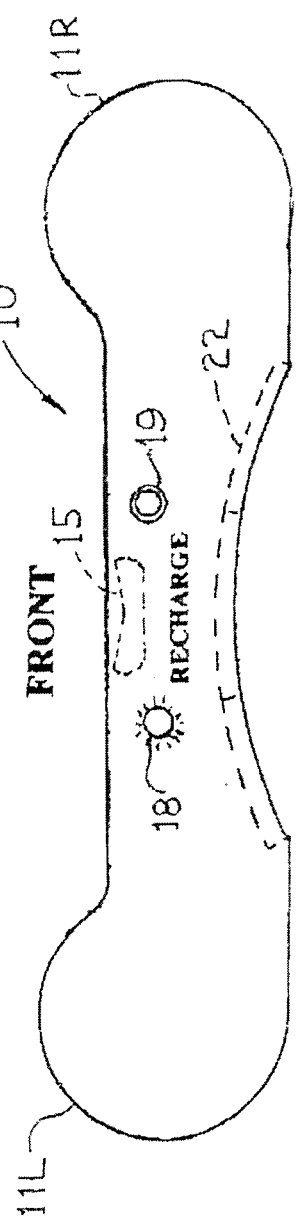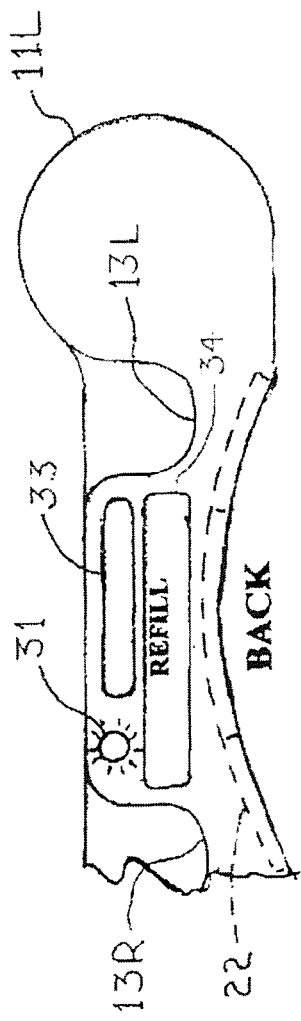

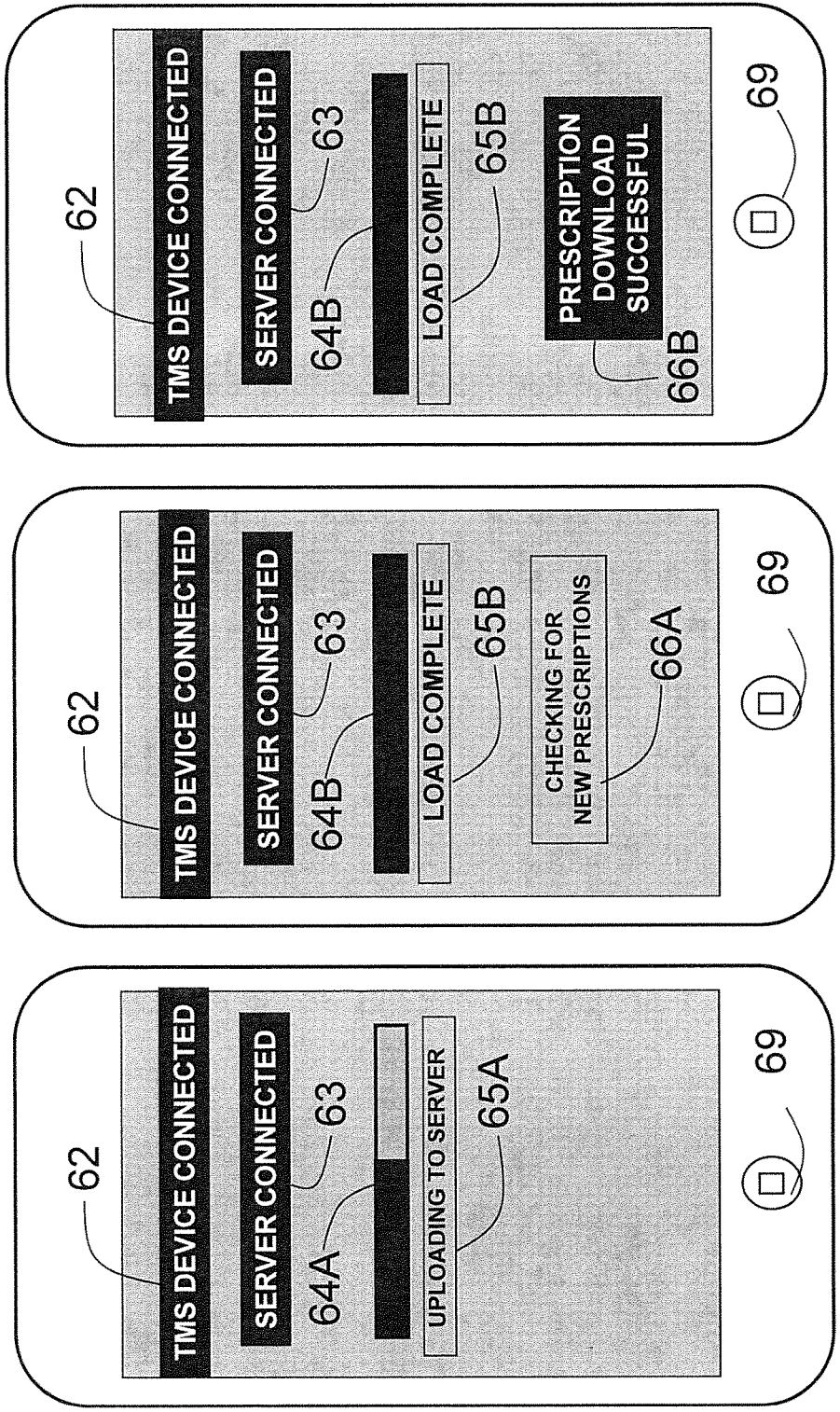

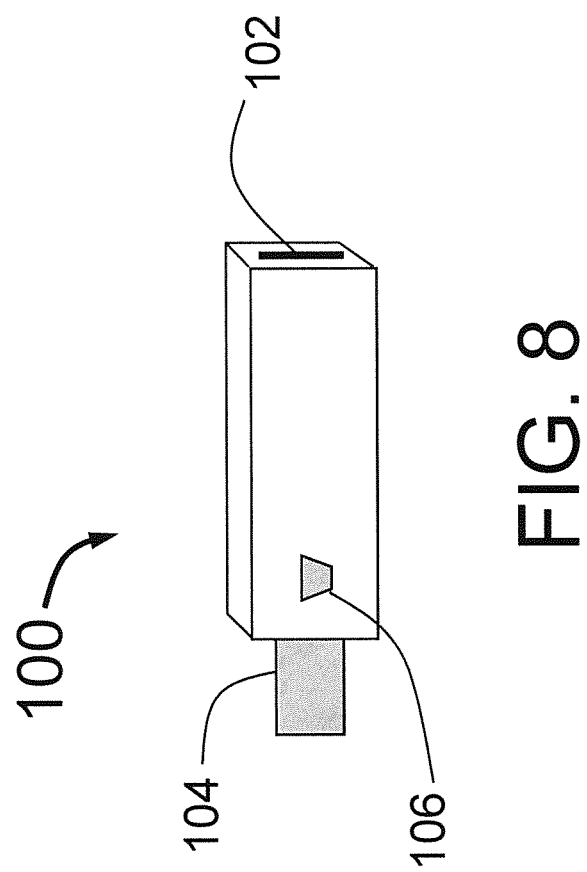

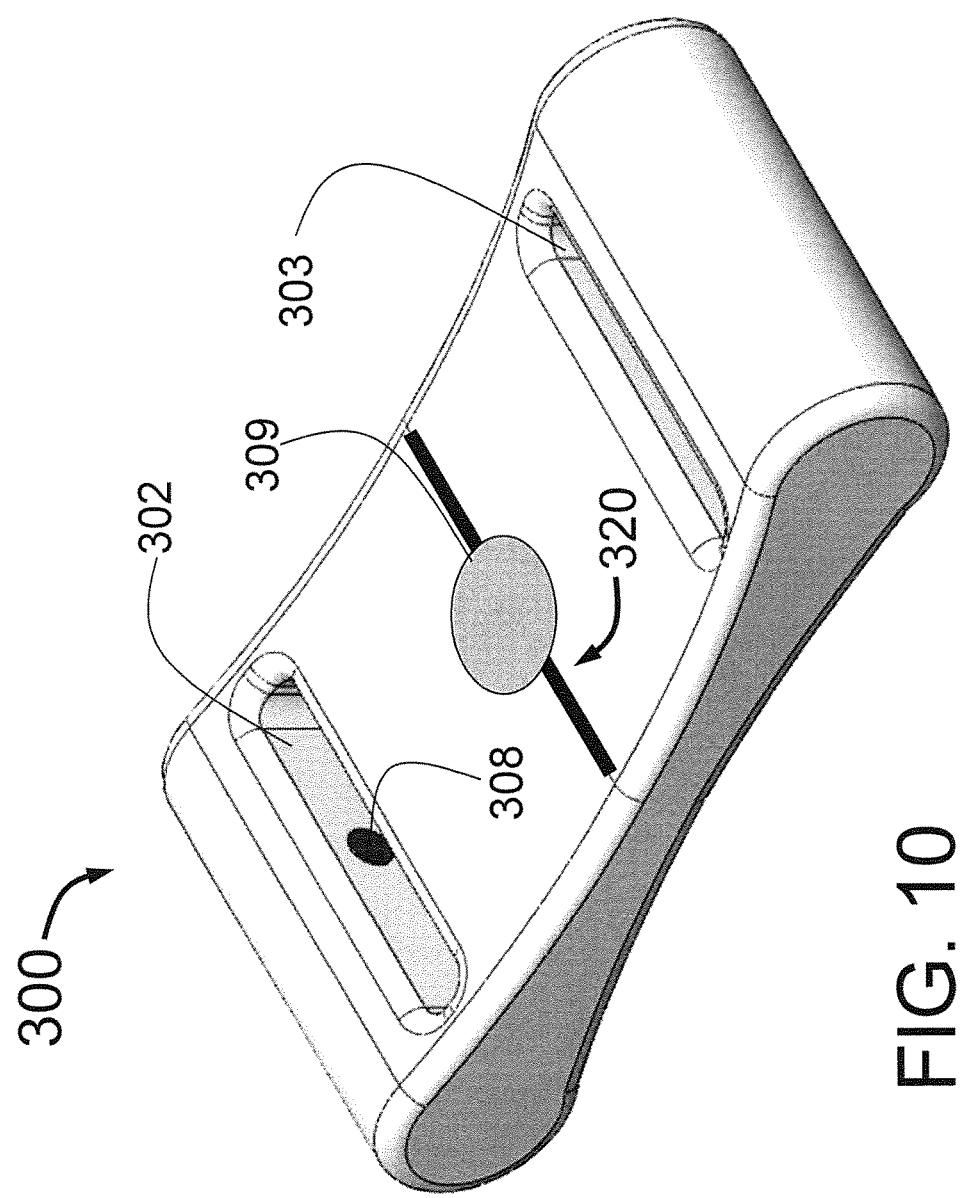

TRANSCRANIAL MAGNETIC STIMULATION DEVICE WITH BODY PROXIMITY SENSORS FOR THE TREATMENT OF MIGRAINE HEADACHES

REFERENCE TO RELATED APPLICATION

This application is being filed as a Continuation-in-Part of patent application Ser. No. 14/147,673, filed 6 Jan. 2014, currently pending.

FIELD OF USE

This invention is in the field of methods and devices that use an intense magnetic pulse to treat migraine headaches.

BACKGROUND OF THE INVENTION

Migraine headaches occur in approximately 12% of the world population. Therefore, in the United States in the year 2013 there are approximately 36 million people who suffer from this affliction. Although medicines have been created that significantly diminish the suffering of migraine patients, these medicines are often contraindicated and have highly undesirable side effects and many patients do not obtain satisfactory relief from the severe headache pain, nausea and other discomforts associated with migraine. Furthermore, migraine headaches are typically treated after they have become painful, i.e., the treatment is often ineffective in preventing the onset of the migraine headache. A non-invasive, non-drug method for the treatment of migraine headaches would be a remarkable boon for those millions of people all over the world who suffer from these painful and often debilitating experiences.

In 1985, A. T. Barker, et al (*Lancet*, 1985, pp. 1105-1107) described the use of a coil placed over the scalp which produced a high intensity, time varying, magnetic field. This time varying magnetic field induces an electric current in the cortex of the human brain which can in turn produce certain effects on the activity of brain neurons. This type of system has been given the name Transcranial Magnetic Stimulation (TMS). If continuously repetitive magnetic pulses are applied in this manner, it has been given the name rTMS. If a single pulse is applied, it has been given the name sTMS. If a treatment includes many pulses, but the pulses are not continuous, even though there are several pulses, this treatment is still called a treatment with a multiplicity of sTMS pulses.

In an article from *Advances in Therapy*, May/June 2001 and entitled "Impulse Magnetic-Field Therapy for Migraine and Other Headaches: A Double-Blind, Placebo-Controlled Study," by R. B. Pelka, et al, there is described a device using an alternating magnetic field source placed on a ribbon around the patient's neck. All devices were no more than 12 inches from the patient's head. The intensity of the 16 Hz magnetic field at the source was 5 microTesla. For all patients, the field at the brain had to be less than 1.0 microTesla. This field was applied for 4 weeks with some benefit being reported in 1 to 3 weeks. The wearing of such a device for weeks is certainly inconvenient as compared to a single magnetic pulse applied for a fraction of a millisecond or at most, a few such pulses. It is also believed that a magnetic field strength of only 1 microTesla would be totally insufficient to erase the aura that precedes many migraine headaches or to be effective to relieve the headache itself.

In the journal *Neurology* (Apr. 11, 2000, pp. 1529-1531) it has been reported by B. Boroojerdi, et al that rTMS at a rate of one pulse per second can create a reduction of the excitability of the neurons of the human visual cortex. However, that article did not indicate that TMS or rTMS can be used for the preventing the occurrence of migraine headaches or diminishing the intensity or duration of a migraine headache.

In U.S. Pat. No. 6,402,678, Robert E. Fischell et al describe means and methods for the treatment of migraine headaches using a portable device that is placed onto the patient's head. This device is used to create a magnetic pulse that acts upon the neurons of the brain and can eliminate both the aura that occurs prior to a migraine headache and a migraine headache after it has started. However, since the entire device is placed onto the patient's head, it is somewhat awkward for the patient's use. Furthermore, since the triggering controls are also located on the head mounted device, their operation is also somewhat difficult.

A device called the "Spring TMS" device has been created by a company called eNeura Therapeutics, LLC and has been used by many patients for the treatment of migraine headaches. Although this device has been very successful for this treatment, it also has several disadvantages. A first disadvantage is that it is quite large and weighs about 4.0 pounds, which makes it somewhat awkward to be carried in a women's shoulder bag or handbag. Still further, it has two movable handles each having two recessed slide operated switches to operate the device and trigger the treatment delivery. The moveable handles complicate the placement of wires that must extend to the slide switches in those two handles for initiating the magnetic pulse. Furthermore, frequent bending of these handles in order to operate the TMS device has the potential to cause wire breakage. Another less than optimum feature of the Spring TMS device is a copper coil having an elliptical shape that is non-optimum for the creation of the desired magnetic pulse from a point of view of its efficiency of converting drive current into magnetic field strength and its weight. The copper coil has a spherical curvature with a radius of 4.5 inches (11.4 cm). The radius of curvature at the top of many human heads appears measure at about 10 cm. Therefore, having a coil to create the magnetic pulse that has a radius of curvature of approximately 10 cm would be much better suited to concentrate the maximum magnetic pulse intensity into the patient's brain. Furthermore, the use of an aluminum coil has the desirable attribute of being lighter in weight as compared to a copper coil that can create the same intensity of magnetic pulse.

Instructions to operate the Spring TMS device are provided by audio cues and further by graphic icons and text messages displayed on an LCD display on the top surface of the device. In the year 2013, the language displayed on the LCD is English. For sales in countries other than those countries where English is the native language, the Spring TMS software must be programmed to provide a language other than English. A maximum of three languages is allowed requiring different firmware for languages beyond the first three. Since there are many countries with large populations of patients having migraine headaches such as Japan, China, India, etc., and in particularly in countries that do not use the Roman alphabet, it would be more cost effective to not require support for the language of every country where the device will be used for the treatment of migraine headaches.

SUMMARY OF THE INVENTION

The present invention is a means and method for improving the treatment of any number of disorders of the brain that can be treated by creating electric currents in the brain by the application of a high intensity, short duration magnetic pulse or a series of such pulses. An example of such diseases includes all types of headaches, depression, obsessive-compulsive disorder, insomnia, bipolar disease, epileptic or febrile seizures and status epilepticus. It is also anticipated that an intense, short duration, magnetic pulse or a collection of pulses could be applied as therapy by stimulation of a variety of nerves such as the occipital nerve or the trigeminal nerve in the region of the head and the vagal nerve in the region of the neck. It is also anticipated that magnetic pulses applied to the carotid sinus and/or vagal nerve in the neck can be used to stop an episode of cardiac arrhythmia such as atrial fibrillation. This invention also envisions the use of the magnetic pulse(s) to prevent the occurrence of such brain and nervous system disorders rather than to merely treat them when they have occurred. As such, periodic use (for example daily use) of magnetic pulses may be beneficial in improving sleep and reducing the incidence of neurological disorders of the brain such as epileptic seizures and migraine headaches. The method of us of the present invention TMS device includes such periodic use and/or responsive stimulation due to the primary symptoms and/or prodromes or auras that occur before the primary symptoms of a neurological disorder of the brain.

For the purposes of this disclosure, the present invention envisions the use of a single TMS pulse or several single TMS pulses. An important use being the treatment of migraine headache, that will be described in detail. However, it should be understood that the system used for the treatment of migraine headache could also be used for the treatment of other disorders such as those mentioned herein. It should be understood that a multiplicity of single magnetic pulses could be used instead of only one pulse. These multiple pulses could either be a multiplicity of single pulses that are spaced apart by several seconds to several minutes, or they could be rTMS which is a continuous train of magnetic pulses. Although the patient will be described in this specification as being of the female gender, it should be understood that the invention can be used by either males or females and by children or adults.

The present invention is a single unit, portable magnetic TMS device that can be placed by the patient onto any region that is in contact with or is placed near her head or any other appropriate place of a human being. This TMS (Transcranial Magnetic Stimulation) device can be powered by a primary battery, a secondary rechargeable battery, from an AC mains receptacle through an AC to DC converter or DC from an airplane's or automobile's commercial power-accessory receptacle. After the device is turned on, a charge switch can be pressed by the patient to begin charging the capacitors to a comparatively high voltage. While charging occurs, a visual display would clearly indicate that the capacitors are charging. Ideally, a line consisting of several light-emitting diode (LED) indicators would turn on from one end of the line to the other indicating the progression of the charging cycle. Alternatively, it is conceived that the TMS device could employ a linear bar that progressively fills with light over time as the capacitors are charged. If for example, only 4 or 5 LEDs are used, then each sequential LED could begin in the off state, then flash and then go solid on. If a multicolor LED array is used, the LEDs could begin in the off state, turn amber and then green. The sequence of LEDs indicating that the capacitors are being charged might ideally have an amber color as an indication of attention, that the capacitors are accumulating the energy needed to create the electrical current pulse in the magnetic coil. When the capacitors are fully charged, a visual indicator, such as an illuminated green LED, would show that the capacitors have accumulated the necessary energy and are now ready to be discharged into a low electrical resistance coil, causing a current to flow, to produce a high intensity, short duration, magnetic pulse. It is highly desirable that the visual display that is used would be of a color intuitively associated with proceeding with the treatment, such as a green light that is used in traffic to indicate "go ahead."

To prevent accidental charging of the capacitors, the charge switch could be under a cover, be a slide or rotary switch, could be recessed below its immediately surrounding surface on the top surface of the TMS device, require activation for a fixed period of time or any other technique that provides a means to prevent inadvertent charging. If the TMS device has an ON-OFF switch that is recessed, and is a type that is difficult to inadvertently turn on such as a rocker switch, then inadvertent charging could virtually never occur since it cannot occur before the ON-OFF switch is turned to the ON position and then, the capacitor charge switch is later activated to charge the capacitors. Similarly, if the TMS device has a combined CHARGE-ON-OFF switch that has stable ON and OFF positions but a momentary (i.e. spring-returned) CHARGE position then inadvertent charging could virtually never occur since it cannot occur before the ON-OFF switch is moved from to the OFF position to the ON position and then later, past the ON position and momentarily to the CHARGE position to activate the charging of the capacitors. Such a three-position switch would preferably be a recessed slide or rocker type. Because it will be valuable for female patients to be able to place their TMS device into their handbags, it is quite important to prevent inadvertent operation of the TMS device when so placed. By having a recessed ON-OFF switch of the slide or rocker design and having a recessed CHARGE switch or a combined-function CHARGE-ON-OFF switch, inadvertent charging of the capacitors would be virtually impossible.

A recently designed TMS device called the "Spring Total Migraine System (TMS) device received CE Mark for sale in Europe in 2011. This device has been used successfully by many Europeans to relieve migraine headaches. However, some problems with that device are its weight, about 4.0 pounds, a size somewhat too large to be placed into a handbag, and moveable handles that include a switch to trigger the magnetic pulse. Requiring wires to pass through a moveable handle to operate the magnetic pulse could also result in some lack of reliability for the Spring TMS device. The present invention is a significant advance by having the two capacitors surrounded by a plastic cover that forms a handle for each hand that can be held by the patient's hands in such a way that the patient's thumb and fingers actually wrap around the cover that surrounds the capacitors. This is a very comfortable way for securely holding the TMS device for easy and accurate placement onto the patient's head and for holding the device in place on the patient's head while waiting for the magnetic pulse to occur.

By not having two handles with two switches to operate the TMS device, inadvertent wire breakage is eliminated and the device's weight and size are somewhat reduced. Still further, the treatment of the patient's migraine headache is further improved by having the magnetic pulse occur automatically at a set time after the green LED light has indicated that the patient should place the device on her head. For example, after the green LED is illuminated and a pleasant sound is created by the TMS device, the patient would have between 4 and 12 seconds to position the TMS device on her head or other place on her body that is the optimum location for her treatment, prior to the delivery of the treatment TMS pulse An optimum time for such placement would be 7±1 second after the LED light turns on. After this time period the treatment would be automatically delivered. This novel concept has several important advantages. The first is that it will not be necessary for the patient to actuate a switch when she wants the pulse to occur. Another advantage is that there will not be a need for another switch on the surface of the TMS device to trigger the magnetic pulse. A third advantage is that if, by some totally unexpected event the capacitors become inadvertently charged, they will automatically discharged in about 7 seconds so that there will be no damage to the capacitors by remaining charged for a long period of time. It is also understood that a pressure or proximity switch could be included that only allows discharge through the coil if the device is touching the head. If not in close proximity to the head, the device could be designed to discharge the capacitors through a resistor instead of through the magnetic coil.

In another embodiment, once the capacitors are fully charged, the TMS device could begin a countdown such as the self-timers on cameras where a LED or light would flash slowly at first then faster then go solid on, and then the pulse would be delivered. A soft tone or a clicking sound that would not aggravate the patient's headache could be used by itself or with the LED light with the same pattern of speeding up, then going steady on just before the pulse is delivered. In this way, once the pattern begins, the patient need only place the TMS device in the appropriate place on the head and wait until the pattern stops and then the pulse would be delivered.

A further improvement on this could include a proximity sensor that would sense that the TMS device is appropriately placed against the head before delivering the pulse or alternatively starting a shorter self timer like count down. Such a head sensor could be an optical, heat, infra-red, pressure, mechanical or capacitive sensor.

Still another preferred embodiment of this concept is a device structure that has finger slots or depressions in the surface that would accommodate the fingers and/or the thumb. A finger sensor in the slots or depressions could be used to sense that the patient's fingers are placed properly and sensing this, the TMS device would deliver a pulse or begin a countdown to allow time for proper placement of the device before the countdown ends and the pulse is delivered. Such a finger sensor could be an optical, heat, infra-red, pressure, mechanical or capacitive sensor.

So the TMS device method of use would be as follows:
1. Use the start button or switch to initiate charging of the TMS device capacitors with associated display.
2. A display light/LED and sound would indicate the capacitors are fully charged and the TMS device is ready to deliver a pulse.
3. The patient would then pick up the TMS device and place it in the appropriate location with the patient's fingers in the slots or depressions
4. The finger sensor when activated by the patient's fingers or thumbs will initiate a short count down with associated sounds. An optional light or display could also blink providing a visual indication of the count down.
5. Such a count down would best be accelerating ticks that then upon delivery of the pulse at the end could also have a different sound played.

Ideally, a finger sensor for each hand would be in the associated slot or depression or finger slot in the case of the TMS device. The TMS device would typically require that both sensors would need to be activated by proper placement of the patient's hands before a pulse could be delivered. Additional programming could allow it for only one hand for disabled patients.

It is envisioned that the time for the count down could be programmable or adjusted with a switch or dial. It is also envisioned that both finger sensors and head sensors could be combined.

If either head or finger sensors if used are not activated within a present period it is also envisioned that a reminder tone could be played so the patient would move ahead to get the pulse delivered. Such a time out could also cause the capacitors to be discharged. In fact, both could be used with a first time out to initiate a reminder and a second time out to turn the TMS device off and discharge the capacitors.

For the purpose of this application, body sensors include head sensors and finger sensors as well as any other mechanical, optical or capacitive sensor that is used to sense proper use or positioning of the TMS device. As such these body sensors each have two states an activated state when the patient's fingers, thumbs or head is sensed and an unactivated state when it is not sensed. If an optical sensor is used then it can be a two piece sensor with a light source and a light detector where blocking the light from the source will cause activation. The optical sensor can also be a photodetector which can sense a change in light without the need for a separate source.

It is also envisioned that a magnetic pulse device as described herein could be used to stimulate other portions of the body and the body sensor could be used to assess proper placement of the device against the surface of the body at the site where the pulse is to be delivered. For example such applications would include stimulating the nerves in the spine to treat pain or the vagus nerve in the neck to treat other neurological disorders.

The high intensity, short duration, magnetic pulse would, by Faraday's Law, induce electric currents in the neurons of the brain (or elsewhere in the body) that would be a treatment for the patient's disorder. For example, if the magnetic pulse was applied to the occipital lobe of the brain during the visual aura before a migraine headache, the aura could be substantially erased and the patient would not progress to having a migraine headache. The magnetic pulse applied to another region of the body could be used to generate an electric current pulse at that location, which electric current pulse could be therapeutic.

An important factor in the design of the TMS device is its ability to limit the number of pulses that the patient could apply to her brain without authorization from the physician who prescribed the device for the patient's use. If there were an unlimited number of pulses that the device could deliver, a patient might inappropriately allow an unauthorized person to use the device without a proper prescription from a doctor. By limiting the number of pulses that could be applied without a refill prescription from the patient's doctor and by charging a moderate amount of money for each pulse that is used, the patient will not be tempted to allow others to use her TMS device without a proper prescription from a licensed physician. It should however be understood that a device which can apply an unrestricted number of pulses is conceived of as included in the concept of the present invention.

A potential safety aspect of this invention is that the TMS device could limit the number of pulses per unit time that the patient could receive. For example, the device could be designed to disallow more than (let us say) ten pulses in any one-hour period.

To satisfy the need for a refill of available pulses and reading data into and out of the TMS device, it could include a wired data communication interface (physical connection port and associated data communication protocol) such as any standard computer input-output connection including, but not limited to, RS-232, USB, Ethernet LAN, IEEE 1394 (FireWire®), Lightening®, etc to connect to a computer which has access to a central server via the Internet. An alternative wired data communication interface could be a custom-engineered connection port with a supporting communication protocol and interface circuitry. An alternative wired data communication interface could use the standard RJ-11 telephone jack supported with a modulator-demodulator (modem) circuit and a communication protocol to communicate digital information over standard land-line telephone voice network to a central server. With such a wired data communication interface as generally described above, the patient could allow the device manufacturer, who controls access to the central server, to add pulses over a connection as allowed by a refill prescription from the patient's doctor. Also, this connection could be used to transmit date and time stamped pulse usage data from the TMS device to the patient's doctor or a central diagnostic center for patient monitoring. The connection could also provide device diagnostics including appropriate information if the TMS device was not operating properly. An alternative means for providing additional pulses and reading data into and out of the TMS device would be by means of a wired USB connection or any other standard type of computer input data communication connection to a personal computer. When a connection is made between the TMS device and a computer, the USB interface could be used to convey an increase in the number of allowed pulses. Of course, any refill of pulses would have to be authorized by a valid and current refill prescription from the patient's doctor or any other authorized medical practitioner.

The USB interface could connect a USB key such as a standard USB thumb drive containing encoded data that will instruct the TMS device to allow a prescribed number of allowed pulses over a predetermined period of time. In any case, the TMS device would be designed so that the USB key would only enable additional pulses one time. Removing and reinserting the USB key a second time would not add additional pulses. In addition, other standard flash memory devices such as a compact flash card, SIM card, memory stick or SD card could be used instead of the USB thumb drive or USB key to add additional pulses for the TMS device.

It is envisioned that other telecommunications interfaces such as wireless data communication could be used instead of a wired connection to reach the central server through the Internet Wireless data communication interfaces include, but are not limited to, 3G/4G cell phone network, IEEE 802.11 (WiFi), IEEE 802.15.1 (Bluetooth), etc. A TMS device incorporating a 3G/4G compatible wireless interface would connect to the central server directly through the wide area network (WAN) commercial cell phone system using a digital data plan. Such a TMS device would be capable of receiving a prescription refill at any time or geographic location with cellular telephone coverage. A TMS device incorporating an IEEE 802.11 (WiFi) wireless interface would connect to a local WiFi router or WiFi hot-spot that is, in-turn, connected to the Internet by a wired or other wireless data communication medium. The WiFi compatible TMS device would connect to the central server and thus also be capable of receiving a prescription refill and exchanging information with the central server. A TMS device incorporating an IEEE 802.15.1 (Bluetooth) wireless interface would connect to a local, near-by, device such as a smart-phone, personal computer, tablet, etc. similarly-equipped with a Bluetooth personal area network (PAN) interface.

A preferred embodiment of the present invention would use a standardized Bluetooth wireless connection between the TMS device and a device such as a smartphone, tablet or PC that is connected to the Internet. An APP or program on the smartphone, tablet or PC would enable both the delivery of new prescription pulses to the TMS device as well as device history and diagnostics to the provider of the TMS device and the patient's physician. Of course any refill of pulses, affected by these wireless communication means, would have to be authorized by a valid and current refill prescription from the patient's doctor or another qualified and authorized medical practitioner.

Because (using one mode of the present invention) there would be a limited number of pulses available to the patient, it would be important for the patient to know the exact number of pulses remaining. To that end, an LCD, LED (or other) display (or audio) could be provided that indicates the number of pulses remaining. If the number of available pulses dropped to that number that would be used by the patient in only a few days, the patient could ask the doctor for a refill prescription or the refill prescription could be on file with the organization that provides a variety of patient services. The patient could then receive a refill from the patient services organization through the telephone connection or by means of the USB key or over the Internet from the central server. It should be understood that once a patient has a previously used USB key, a refill could be accomplished by the use of the USB slot in a personal computer that is connected over the Internet to the TMS device manufacturer (or an authorized service organization) who could verify the refill prescription and the source for payment for the pulses and send the properly encoded data to the USB key to permit additional pulses. The patient would then remove the updated USB Key and insert it into the TMS device to add the prescribed number of pulses and time duration during which time the device would function.

It is also understood that the USB key could be sent by mail or purchased at the patient's local pharmacy. It should also be understood that a date and time stamped history of the number of pulses used could be made available to the doctor or the manufacturer by means of the telephone connection or the USB interface from data stored in a digital memory in the TMS device. The USB interface would work by either connecting using a cable to a personal computer or by transferring the data to the USB key which is then inserted in a the USB slot of a computer connected to the Internet.

It should be further understood that the TMS device system could include a self-checking means that would verify that the magnetic pulse was within a specified limit of amplitude and time duration. This could be accomplished by a separate wire coil located near the device's magnetic coil that would measure the amplitude and time course of the magnetic pulse. If either the amplitude or time course of the magnetic pulse were out of their specified limits, the magnetic TMS device system could produce an error signal that would be detected by the patient and could also be determined by a patient's service center via a telephone or Internet connection. The warning could be by means of a visual display or by means of a voice warning. Additionally, the patient could be provided with a separate device that could be used to check the amplitude and time course of the magnetic pulse. This could be an external device onto which the patient places the TMS device, then actuates the TMS device and then the external device measures the magnetic pulse. It is also envisioned that a closed-loop control system could be used where the level measured on the previous pulse could be used to change the charge parameters on subsequent pulses to maintain the magnetic pulse within pre-defined limits. Such calibration could be manual (such as a "calibrate" button) or automatic, done each time the TMS device pulses.

Another important aspect of the invention is that each TMS device would have a unique serial number that is recorded for a particular patient. When the TMS device transmits the stored data on pulse usage or receives instructions to add pulses, the data transmitted to and from the TMS device must be encrypted so that it would be essentially impossible for an unauthorized person to add pulses to the TMS device or to gain access to the patient's use of pulses to treat her brain (or other) disorder. Furthermore, a secure link could allow the patient to be recognized only by her serial number so that her actual name would not be known to the operator at the manufacturer's service center. Thus patient confidentiality would be maintained. An optimum serial number for a patient could be that patient's three initials followed by a number that would be the greatest number of patients that would ever be expected to have those three initials. For example, the first patient having the initials AAA would also have the numbers 00001 added after those initials so that her serial number would be AAA00001. This type of serial number would therefore accommodate one hundred thousand patients all having those same three initials. If the patient would have more than three names, then the three initials to be used would be the first letter of the first, second and last name. For hyphenated last names, the first letter of the first name and each of the two letters of the hyphenated name would be used. If the patient had only two names, then the initials of the first and last name would be used with the letter "N" placed in between.

This type of serial numbers would be used only for patients in a country that uses the Roman alphabet and numbers as used in the United State of America, North and South America, the majority of the European Union, and Australia. For patients in any other country that does not use that alphabet, an eight digit serial number consisting entirely of numbers would be used. Of course having eight numbers would allow essentially one billion patients to have a different serial number.

Another important aspect of the present invention is the shape and material of the magnetic coil. In U.S. Pat. No. 5,116,304, J. A. Cadwell describes a magnetic coil that has the shape of a skullcap. Cadwell states that this coil can be made from "litz wire or copper strip wire" but he never envisages aluminum wire with a rectangular cross section which is optimum for a TMS device because of its low electrical resistance with significantly reduced weight. Also, the cost of aluminum wire is distinctly less than the cost of litz wire whether the litz is formed from copper or aluminum. The optimum shape for the aluminum wire coil is in the shape of a spherical sector that somewhat matches the spherical curvature of the head. Measurements have indicated that the radius of the spherical sector should be approximately 10±1 cm. The optimum arrangement of the aluminum wire having a rectangular cross section is to have the long extent of the rectangular wire being situated generally vertically outward from the patient's head.

An additional feature of the present invention is to "pot" the coil by encapsulating it in plastic. This will reduce the noise produced by wire movement when the pulse is delivered as well as prevent unwanted motion of the coil wires, which will improve the longevity of the coil. In addition to reducing the acoustic signature of the energized TMS coil, potting also provides high-voltage electrical insulation to reduce electrical breakdown.

An important feature of the TMS device is a first audio signal means to indicate to the patient that the capacitors have been fully charged and the patient should place the device on her head and a second audio signal that will indicate to the patient that the magnetic pulse has occurred. Ideally, each of these pulses will occur for a time period between 1 and 2,000 milliseconds. Ideally these pulses would be different from each other so that they will be associated with two different events. It should be understood that these pulses could be a single tone or multiple tones or even a collection of musical notes. It should be understood that these sounds could be pre-recorded audio clips, selected from a catalog of such sounds and downloaded into the device through the data communication interfaces previously described. For example the favorite or sentimental ring tones on your cell phone could personalize it for any patient. It should also be understood that the audio signal could be a voice that has an announcement that the capacitors are charged or the statement, "place the device on your head," and the statement, "the pulse has been delivered," could occur after that event has occurred. The language used for the vocal announcements would ideally be in the language of the country where the device was prescribed.

Thus one object of the present invention is to have a magnetic TMS device that is portable and operated by the patient for the treatment of disorders of the brain, the TMS device being designed to provide one or more, high intensity, short duration, magnetic pulses that are applied to the neurons of the brain or to any other body part that is to be treated, the purpose of the treatment being to prevent the pain, photophobia, phonophobia and/or nausea associated with a migraine headache or any other disorder that can be prevented or ameliorated by the use of sTMS (which is the same as TMS) or rTMS.

Another object of this invention is to limit the total number of pulses available before a refill takes place and also to limit the number of pulses allowed in a predefined time period.

Still another object of this invention is to have the availability of additional magnetic pulses provided by means of a telephone (or Internet) connection or from a USB key, SIM or memory card from an authorized provider of the pulses and based upon a refill prescription from the patient's doctor.

Still another object of this invention is to have the refill data message in an encrypted format so that a refill of pulses cannot be accomplished without proper authorization.

Still another object of this invention is to have a curved, spherically shaped coil for the TMS device that can create a magnetic pulse over either or both sides of the occipital lobe of the brain, the radius of curvature of the sphere sector being approximately 10±1 cm.

Still another object of this invention is to have a visual display on a TMS device that can show the number of pulses remaining, the status of the capacitor charging cycle and that the capacitors are fully charged.

Still another object is to have a display that indicates the remaining capacity of the internal battery pack Still another object of this invention is to have a means to prevent inadvertent activation of the charge switch that starts the capacitor charging cycle.

Still another object of this invention is to have the visual displays be designed as to color (viz, red, amber, green, etc.) and intensity to minimize discomfort for a person experiencing a migraine headache, which patient may be undergoing photophobia, i.e., a high sensitivity to light.

Still another object of this invention is for the TMS device to have an access port for accessing the location of the rechargeable battery so that battery replacement is simplified.

Still another object of this invention is to have a covered access port for a SIM card, which SIM card provides a serial number for the TMS device and the SIM card can also have the capability to set the number of pulses allowed and the time duration allowed for the TMS device to continue to function.

Still another object of this invention is to have a potted coil that will reduce the sound generated by coil wire movement when the pulse is delivered as well as increase the longevity of the coil.

Still another object of this invention is to have a "self timer" that begins automatically when the capacitors are charged and will activate the pulse after a count down allowing the patient time to properly place the TMS device onto her head for pulse delivery.

Still another object of this invention is to provide a wireless connection though a smartphone, tablet or PC to allow new prescriptions to be downloaded to the TMS device and device diagnostic data and patient use data to be uploaded to the TMS device provider and the patient's physician.

Still another object of this invention is to include sensors for the patient's fingers and thumbs that would not initiate a countdown to a pulse until the TMS device is properly grasped.

Still another object of this invention is to include a head sensor that will not allow delivery of a pulse if the TMS device is not placed against the head. Such a sensor could also be the trigger to initiate a pulse or initiate a countdown to delivery of a pulse.

Still another object of this invention is to have time outs in the programming that can if activated, initiate a reminder to the patient and/or shut the TMS device down.

Still another object of this invention is to have a body proximity sensor that can be used for non-invasive magnetic pulse stimulation of any portion of the body.

Still another object of this invention is to include a method of treatment that includes use of the TMS device in one or more of the following ways:
1) Responsive to the aura or prodrome that occurs before the primary symptoms of a neurological disorder;
2) Responsive to the primary symptoms of a neurological disorder;
3) Periodic stimulation on a scheduled basis Still another object of this invention is to include a method for responsive and/or periodic stimulation of one or more single pulses from a TMS device for the treatment or prevention of one or more of the following:
1) Migraine Headaches;
2) Epileptic Seizures
3) Cardiac Arrhythmias
4) Sleep Disorders Still another object of the present invention is to include a method of improving sleep by periodic stimulation one or more single pulses from a TMS device.

The term application program includes APPs that run on a smartphone or tablet as well as a program that runs on a personal computer.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 3 is a front side view of the TMS device showing the LED that indicates the device needs to be recharged and the receptacle for the placement of a power cord to recharge the TMS device.

FIG. 4 is a partial back side view of the TMS device showing the position of the LED that would indicate that the device should be refilled with magnetic pulses because either the total number of pulses is nearing its maximum allowed number or the time limit has been reached when the TMS device will cease to operate, and also showing the cover over the location where a SIM card would be placed and where the USB connection can be made.

FIG. 7C shows the wording that would come up on the smart phone showing that the central server is being connected to the TMS device.

FIG. 7D shows the wording that would come up on the smart phone showing that the loading of the server has been completed and the smart phone is checking to see if there is a new prescription for the patient.

FIG. 7E shows the wording that would come up on the smart phone showing that a prescription download has been successfully placed into the TMS device.

FIG. 8 illustrates an adapter that allows a SIM card to be connected to the TMS device's USB interface.

FIG. 10 illustrates an embodiment of the present invention TMS device showing the bottom of the device including finger sensors and a head sensor.

DETAILED DESCRIPTION OF THE INVENTION

Figure 1:
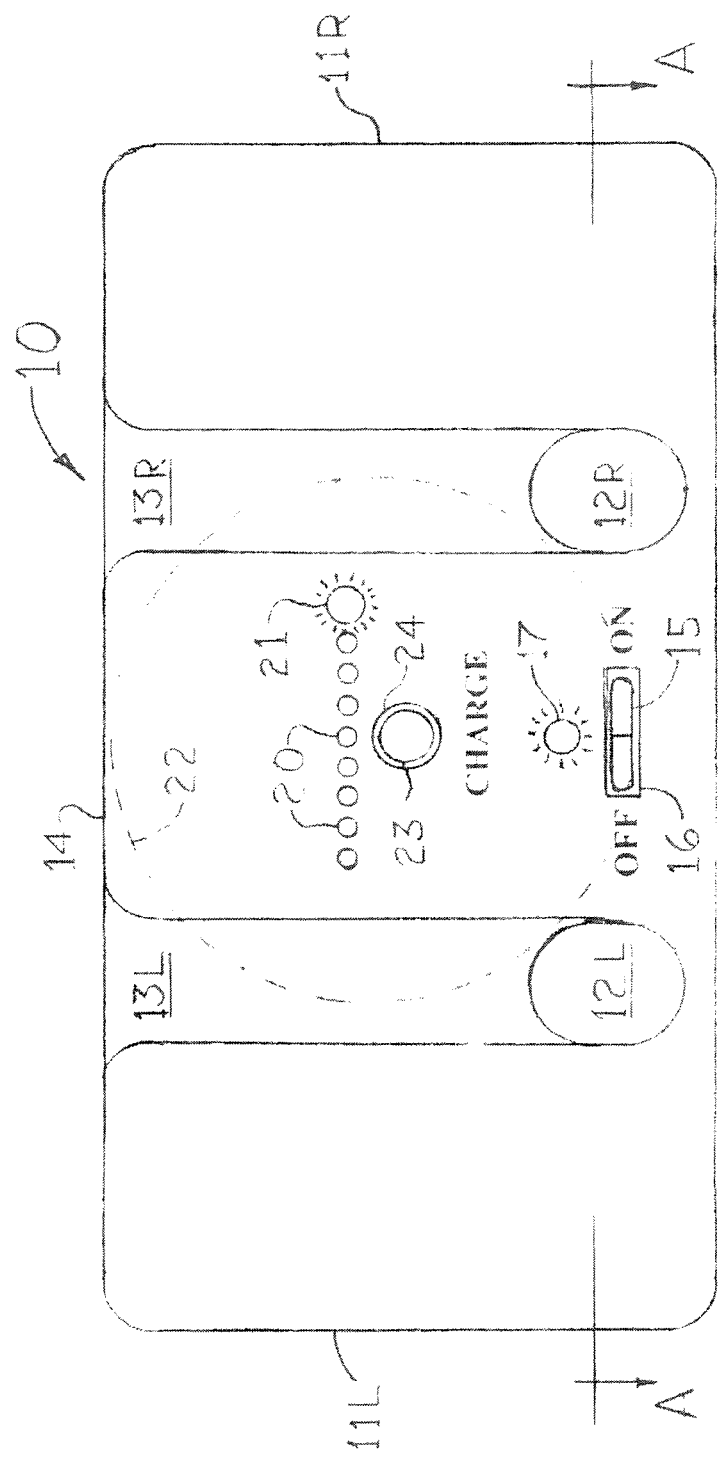
FIG. 1 is a top view of the magnetic TMS device system for the treatment of disorders of the brain or other body tissues or organs.

FIG. 1 is a top view of the TMS device 10 having a left cylindrical portion 11L and a right cylindrical portion 11R around which portions the patient will hold the TMS device

Figure 2:
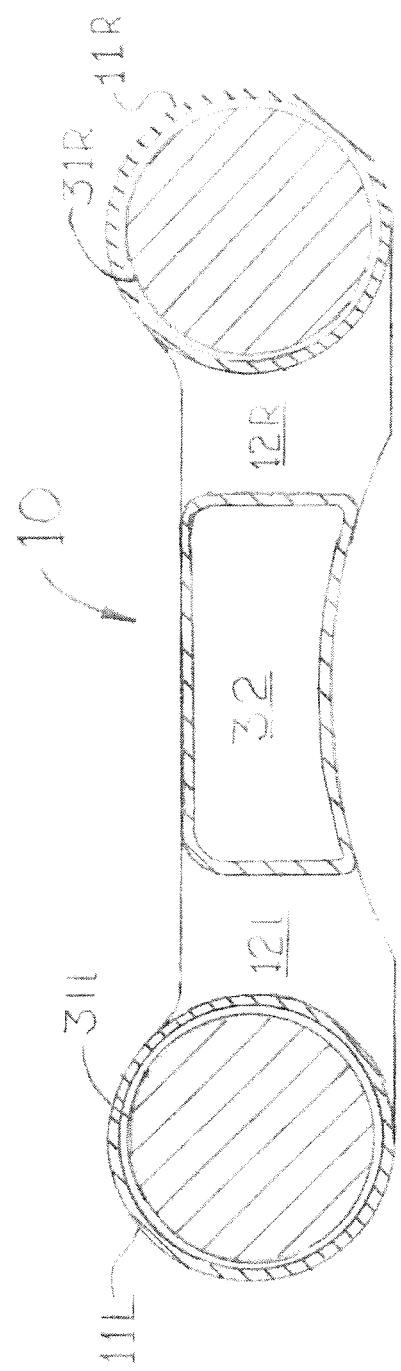
FIG. 2 is a cross section of the TMS device at section "A-A" of FIG. 1.

10. FIG. 2 is a cross section of the TMS device 10 at section "A-A" of FIG. 1. As seen in FIG. 2, within the left cylindrical portion 11L is the left capacitor 31L and within the right cylindrical portion 11R is the right capacitor 31R. The top view of the TMS device 10 also shows the left fingers groove 13L, the right fingers groove 13R, the left thumb hole 12L and the right thumb hole 12R all of which are shaped to provide a comfortable and secure means for the patient to hold the TMS device 10 when she places it on her head for the treatment of a migraine headache.

FIG. 1 also shows an ON-OFF switch 15 in an ON-OFF switch recess 16. The ON-OFF switch 15 is used to turn the TMS device 10 on or off. When the ON-OFF switch 15 is pushed downward on its right side, it is in the ON position. When that occurs, an LED light 17 turns on to indicate that the TMS device 10 has been turned on. It would be typical for the LED light 17 to have an amber or green color to indicate that the device is ready to charge its capacitors 31L and 31R. The ON-OFF switch 15 would be pushed down on its left side to turn the TMS device 10 off. The ON-OFF switch recess 16 is provided to decrease the possibility that the ON-OFF switch 15 would be inadvertently turned to its ON state. The recess placement of the ON-OFF switch 15 also disallows it being turned off when the ON state is desired.

As seen in FIG. 1, the top surface of the TMS device 10 would also have a capacitor charge switch 23 to cause the battery (not shown) to begin the charging of the capacitors 31L and 31R. The capacitor charge switch 23 would be within the charge switch recess 24 so that it is under the top surface of TMS device 10 to prevent the accidental pushing of the capacitor charge switch 23. By having both switches 15 and 23 on the top surface of the TMS device 10 placed respectively within the recesses 16 and 24, accidental actuation of either of the switches 15 or 23 would be prevented. This is particularly important to prevent the TMS device 10 from being inadvertently turned on when it is placed inside a woman's handbag.

When the capacitor charge switch 23 is pushed down to charge the capacitors 31L and 31R, a series of LED lights called the capacitor charging lights 20 will illuminate in sequence to indicate that the capacitors 31L and 31R are being charged. The optimum color for the capacitor charging lights 20 is probably amber which indicates that the patient should get ready for the (preferably) green LED capacitors charged light 21 to turn on which indicates that the capacitors 31L and 31 have been fully charged and are ready to be discharged into the spherical cap coil 22. The circular outline of the spherical cap coil 22 is shown by dotted lines in FIG. 1. The sequence of lighting the LED lights 20 could be on a timed basis or they could be triggered by the capacitors 31L and 31R reaching a specific and increasing voltage. An example of the time dependence of the lighting of the capacitor charging lights 20 would be if it would take 40 seconds to charge the capacitors 31L and 31R and if there were exactly ten capacitor charging lights 20, then each additional amber LED light 20 could come on at 4 second intervals until all ten of the capacitor charging lights 20 were turned on. When the last amber LED light 20 would light, (that LED light 20 next to the green LED light 21) then simultaneously the green capacitors charged light 21 would come on, or the capacitors charged light 21 could come on 4 seconds after the last amber LED light 20 comes on. In either case, when the green LED light 21 would come on, that indicates that the capacitors 31L and 31R have been fully charged. Once the capacitors 31L and 31R are fully charged, they are ready to be discharged into the spherical cap coil 22 to create the intense magnetic pulse to treat a migraine headache. As an additional indication to the patient that the capacitors 31L and 31R have been fully charged, a sound generator (not shown) within the TMS device 10 would create a sound that last from as short as 0.001 second to as long as 2 seconds as an additional indication to the patient that the capacitors 31L and 31R have been fully charged. An optimum sound would last approximately 1±0.5 second and would have a pleasant single tone or it could be a musical type of sound.

In one embodiment, once fully charged the TMS device could begin a count down such as is seen on self-timers on cameras where the green LED 21 would flash slowly at first then faster then go solid on, then the pulse would be delivered. A soft tone or a clicking sound that would not aggravate the patient's headache could by itself or with the LED utilize the same pattern of speeding up, then going steady just before the pulse is delivered. In this way, once the pattern begins, the patient need only place the TMS device in the appropriate place on her head and wait until the pattern stops, the green LED 21 stays continuously on and the pulse is delivered.

FIGS. 1, 2 and 4 indicate the novel means that the TMS device 10 would utilize for the patient to hold that device against her head for the treatment of a migraine headache or any other disorder originating from her brain or any other part of her body. It should be understood that the TMS device 10 could be used to apply a magnetic pulse to any part of the human body where the application of that magnetic pulse could be effective in the treatment of some medical problem.

FIG. 2 is the cross section of the TMS device 10 at section "A-A" of FIG. 1 showing the left cylindrical portion 11L, the right cylindrical portion 11R, the left capacitor 31L, the right capacitor 31R, the left thumb hole 12L, the right thumb hole 12R, and an electronics and battery section 32. FIG. 4 is a partial side view shown from the back of the TMS device 10. From these three FIGS. 1, 2, and 4) it will be apparent to a person of ordinary skill in this art that this is a novel and efficient means for the patient to securely and comfortably hold the TMS device against her head for the treatment of a migraine headache.

From FIGS. 1 and 4 it is clear to see that as many as four of the patient's fingers (other than her thumb) of her left hand could be placed in the left fingers groove 13L and the right hand fingers could be simultaneously placed in the right fingers groove 13R. At that same time, FIGS. 1 and 2 show that the patient's left thumb could be placed through the left thumbhole 12L and her right thumb could be placed through the right thumbhole 12R. This novel and useful means for holding the TMS device 10 allows the patient to place the TMS device 10 securely onto her body wherever treatment with a strong magnetic pulse would ameliorate some health problem. Most importantly, placement of the TMS device 10 onto the patient's head or neck would be for the treatment of a migraine headache.

An important and novel feature of the present invention is the absence of a switch to trigger the discharge of the capacitors 31L and 31R into the spherical cap coil 22 to create an intense, short time duration, magnetic pulse. This TMS device 10 would be designed to have the patient place the device on her head for the treatment of a migraine headache at some reasonable time (greater than 2 seconds) after the capacitors charged light 21 is turned. A time period of about 7±1 seconds after the LED green light 21 comes on would be an optimum time period for the patient to comfortably place the TMS device 10 onto her head. At that time, the electric current in the spherical cap coil 22 would produce the desired intense magnetic pulse. The maximum pulse intensity at the center of the spherical cap coil 22 should be greater than 0.2 Tesla and optimally the maximum pulse intensity should be 1.0±0.5 Tesla. The pulse rise time should be between approximately 100 and 300 milliseconds with an optimum time being 190±10 milliseconds.

Although it is understood that a 7 second time delay may be optimum, it should be understood that any time period between approximately 2 and 60 seconds could be used as a time interval from the time that the LED light 21 goes on until the magnetic pulse is actuated to treat the patient. Any time period that is less than approximately 2 seconds would be too short a time interval for the patient to feel comfortable in getting the TMS device 10 properly placed onto her head.

A very important design feature of the present invention is that a sound would be created by the TMS device 10 at the same time that the TMS pulse is delivered. This sound could last for a time period between 0.001 second and 2 seconds with an optimum time being approximately 1±0.5 seconds. The importance of this sound is that it indicates to the patient that a magnetic pulse that is within the specified intensity limits for the TMS device 10 has been delivered. If either the amplitude or the pulse rise time of the TMS delivered by the spherical cap coil 22 is not within its specified limits, then no sound will be created and the patient will know to contact the manufacturer to obtain a new TMS device 10. The detection of pulse amplitude and pulse rise time will be made by a small coil placed at or near the center of the spherical cap coil 22.

An additional feature of the present invention is to "pot" the coil 22 by encapsulating it in plastic. This will reduce the noise produced by wire movement in the coil when it is energized to deliver a pulse. Potting the coil also prevents unwanted motion of the wires of the coil 22, resulting in improved the longevity of the coil.

After the magnetic pulse is actuated, the device will remain in the ON condition but the LED lights 20 and 21 will go to an off condition. The patient can get another pulse by once again pressing the capacitor charge switch 24, the LED lights 20 will then illuminate sequential approaching the green LED light 21. When the light 21 is illuminated, the timing circuit will start the time period to cause the magnetic pulse to occur. When the patient takes the last of a sequence of magnetic pulses, she will press down on the left side of the ON-OFF switch 15 to turn off all the circuits of the TMS device 10.

FIG. 3 is a front surface view of the TMS device 10 and FIG. 4 is a partial view of the back surface of the TMS device 10. FIG. 3 shows a battery needs recharging light 18 that would indicate to the patient when the battery in the TMS device 10 will need to be recharged. It would be typical for the battery in the TMS device 10 to have a sufficient capacity to provide about twenty magnetic pulses. An optimum LED light 18 would be a light that flashes on and off at about a 0.5 second period when there is enough capacity left in the battery to provide between 5 and 8 magnetic pulses. The battery needs recharging LED light 18 would remain steadily on when there would be between 1 and 4 pulses remaining before the battery is completely discharged. That LED light 18 would remain on if there was no capacity left in the battery and the ON-OFF switch 15 was in the ON condition. It is also understood that the LED light 18 could have a red or any other color that would signify the need for the battery to be recharged. Recharging of the battery within the TMS device 10 would be accomplished by means of a separate recharging device (not shown) that includes an AC-to-DC convertor and wire with plug (not shown) as is typically used to recharge any portable device such as a cell phone or a tablet. Such a recharging device would have a plug that would fit into the battery recharge receptacle 19 that is shown in FIG. 3.

FIG. 4 is a partial view from the back of the TMS device 10. As described above, FIG. 4 shows the left finger groove 13L and part of the right finger groove 13R. It is into these grooves that the patient could place 3 to 4 fingers (but not the thumb) to securely hold the TMS device 10 when it is placed onto the patient's head. FIG. 4 also shows the prescription refill needed LED 31 that would flash with a time period of approximately 0.5 seconds when there are only approximately 17 to 32 pulses still available before the doctor must provide a refill prescription or only 14 days remain until the end of the time period during which time the TMS device 10 would remain operable. The prescription refill needed light 31 would remain steadily on when there are 16 or fewer pulses remaining before the TMS device 10 becomes inoperable or there are only 7 or fewer days left until the TMS device 10 becomes inoperable. With these warnings, the patient would know that she must contact her doctor to receive a refill prescription.

The prescription refill port 33 is used by the patient to accommodate a refill of her prescription for magnetic pulses, which refill prescription must come from her physician or any other person legally entitled to write a prescription. Unlike other refill prescriptions written on a piece of paper that a patient could typically receive from a doctor to obtain an additional dose of pills, the refill prescription for the TMS device 10 would be delivered electronically or by means of radio frequency (RF) communication or by means of a SIM card that is placed into the TMS device 10 through the port 33. The SIM card can also be used to provide a unique serial number for each patient.

A refill prescription for each patient would increase the number of pulses as prescribed by the patient's doctor and would also extend the time period during which time period the device will remain in a condition where it can be turned to its ON state and can be used to deliver a magnetic pulse. As an example, if a patient would have four migraine headaches each month and would use ten magnetic pulses to treat each headache, then she would use forty pulses per month and 240 pulses in a six-month period. For such a patient, a physician might prescribe 250 pulses over a six month period with the TMS device 10 going to its off condition if either the 251st pulse was requested or the 6 month time period had expired. Before either of those events would occur, the LED light 33 would start flashing and later turn steadily on as a warning to the patient to promptly obtain a refill prescription from her doctor. It would be desirable for the LED light 31 to have a color that is different from the colors chosen for the LED lights 17, 20 and 21. It could be desirable for the LED lights 18 and 31 to have the same color, as each would indicate to the patient that some action must be taken.

FIG. 4 also shows a battery access door 34 that could be opened to access the battery (not shown). In this way, a failed battery could be readily replaced. It is typical for a device such as the TMS device 10 to have its battery fail prior to any other part of the device failing. Therefore, an easy means to accomplish battery replacement would be highly desirable.

Figure 5:
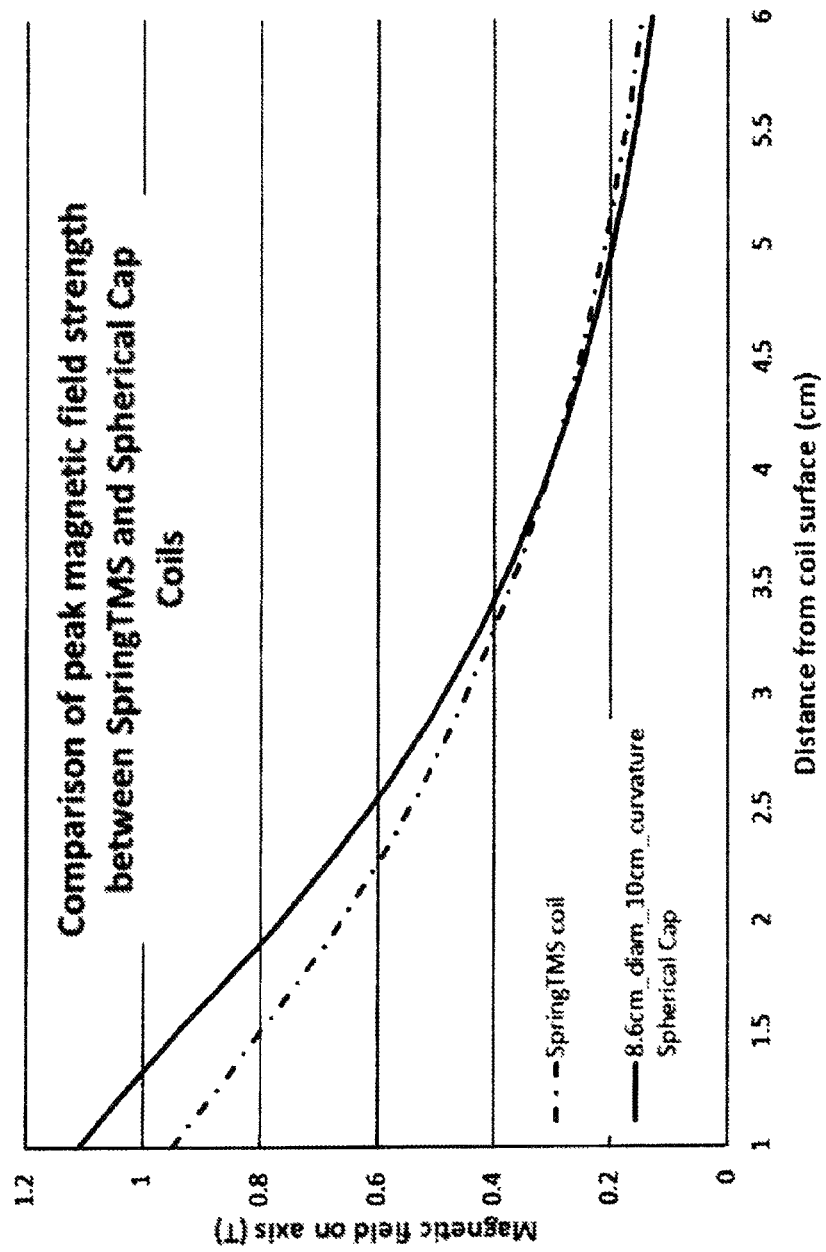
FIG. 5 illustrates the fall of magnetic field strength with distance from the center of the Spring TMS coil and the center of the spherical cap coil.

FIG. 5 shows the falloff of magnetic field intensity as a function of distance from the bottom surface of the spherical cap magnetic coil as compared with that same magnetic field intensity for a prior design (the Spring TMS device) that has an elliptically shaped magnetic coil. This field strength measurement indicates that a smaller, lighter, aluminum wire coil can produce essentially the same magnetic field strength as compared to a heavier, elliptically shaped copper coil that has been used in a prior art design TMS Devices device. It is urgently important that the magnetic coil 22 be potted in plastic to extend its useful life and to avoid the sound that might otherwise emanate from the coil 22 if the wires were free to move.

Figure 6:
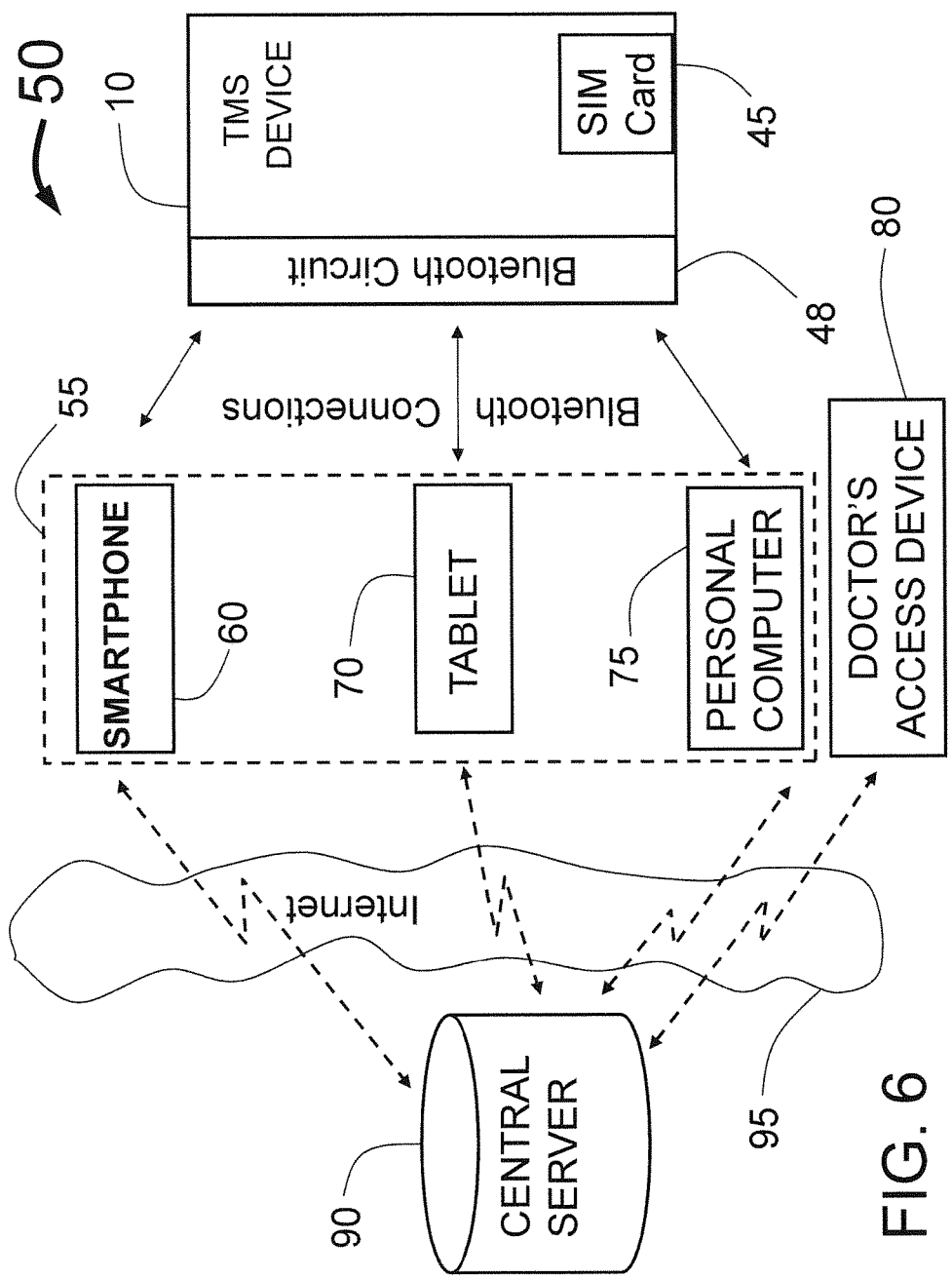
FIG. 6 is a flow chart showing the flow of information among the various portions of the TMS system to provide a refill prescription for a migraine patient.

FIG. 6 is a block diagram of the TMS device system 50. The system 50 includes a computational device 55 with Bluetooth data communications capability as well as the ability to connect to the Internet 95. The computational device 55 is kept by the patient and may be, for example, a smartphone 60, tablet 70 or personal computer 75. The system 50 includes the TMS device 10 having a SIM card 45 and wireless circuit 48. The wireless circuit 48 may be cellular wireless data, WiFi (a, b, g or n) or Bluetooth. Bluetooth is a well-known standard for short range data communication between computational devices 55 which include (but are not limited to) personal computers 75, cell phones and tablets 70 and their accessories. Bluetooth and WiFi capabilities are built into most cell phones including smartphones 60 which include i-Phones, Android phones and Blackberry cell phones. Bluetooth communication capability is also built into most tablet computers and personal computers (PCs). Add-on Bluetooth circuits are also available for personal computers 75.

If WiFi is used for the wireless connection, then the TMS device 10 would connect through a local router to the smartphone 60, tablet 70 or PC 75 or directly to the Internet. If the wireless connection is a cellular data connection then no local router is needed and the TMS device 10 can connect through the cellular data network to the Internet.

WiFi or cellular data would allow communication directly between the TMS device 10 and the central server 90 without the need for a smartphone 60, tablet 70 or PC 75. In this case, the TMS device 10 would include the application/program to facilitate downloading new or changed prescriptions and uploading of diagnostic data and patient use data between the TMS device 10 and the central server 90.

The remaining descriptions will describe the procedure of downloading new prescriptions to the SIM card 45 in the TMS device 10 using Bluetooth as the wireless connection although similar functions can be applied if WiFi is used to communicate between the TMS device 10 and a smartphone 60, tablet 70 or PC 75.

Typically, the prescription information, number of pulses or time remaining (and/or used), patient use information and device diagnostic information would be stored in flash memory on the SIM card 45. Patient use information would include, for example, the time and date for each pulse delivered by the TMS device 10. Device diagnostic information would include (but is not limited to) battery condition, magnetic pulse strength and pulse shape for each delivered pulse, any faults in device operation, etc.

Once a Bluetooth connection between a computational device 55 and an accessory is set-up and enabled for automatic connection, turning on the accessory power within range of the Bluetooth antenna in the computational device 55 will automatically cause the connection to be established.

The system 50 also includes a central server 90, which includes patient prescription information and can also be used to keep patient use information and diagnostic information uploaded from the TMS device 10. The central server 90 is also connected to the Internet 95.

The system 55 also includes a doctor's access device 80 which can connect through the Internet 95 to the central server 90. This would allow the patient's doctor or his staff (nurse practitioners or professional assistants) to write prescriptions for additional time to remain active and additional pulses for the TMS device 10 which when transferred to the SIM card 45 on the TMS device 10 will provide the patient additional time (e.g. 6 months) or pulses (e.g. 300 pulses) to be used to treat the patient's migraine headaches. The doctor's access device 80 could also access patient use information and diagnostic information downloaded from the TMS device 10 to the central server 90. The doctor's access device 80 can be a personal computer, tablet or smartphone that has Internet connectivity and a browser that allows standard Internet access. Access to write prescriptions on the central server 90 can be through html or other web pages or with a specific program that can run on the doctor's personal computer or an APP that can run on the doctor's smartphone or tablet. Appropriate security with appropriate login and passwords would be required to allow prescriptions to be written. This security could be obtained by using a specific serial number for the TMS device 10, which serial number could originate from the SIM card 45.

It is also envisioned that the central server 90 would have the ability to communicate the writing of a new prescription to the patient's insurance company for reimbursement or to bill the patient's credit card. An e-mail indicating that a new prescription is available can be sent to the patient including a receipt for payments if the patient is paying or confirmation of insurance reimbursement if the insurance company is paying. A phone call or SMS message (standard text message) could also be used to notify the patient.

FIGS. 7A through 7E inclusive illustrate features of a smartphone 60 that would be one of the means to write new prescriptions into the patient's TMS device 10. The smartphone 60 has a main button 69 to download a new prescription from the central server 90 to the TMS device 10 as well as upload patient use and device diagnostic information from the TMS device 10 to the central server 90.

Once the patient knows that a new prescription to provide additional time and/or additional pulses for the TMS device is ready to be sent to her, she can download the prescription to the SIM card 45 on her TMS device 10 in the following way:

1. Assuming the smartphone 60 is turned on, turn on the TMS device 10, which connects via Bluetooth to the smartphone 60.
2. Initiate the TMS APP. For most smartphones 60 and tablets 70, one simply touches the TMS APP icon 61 shown in FIG. 7A.

Figure 7B:
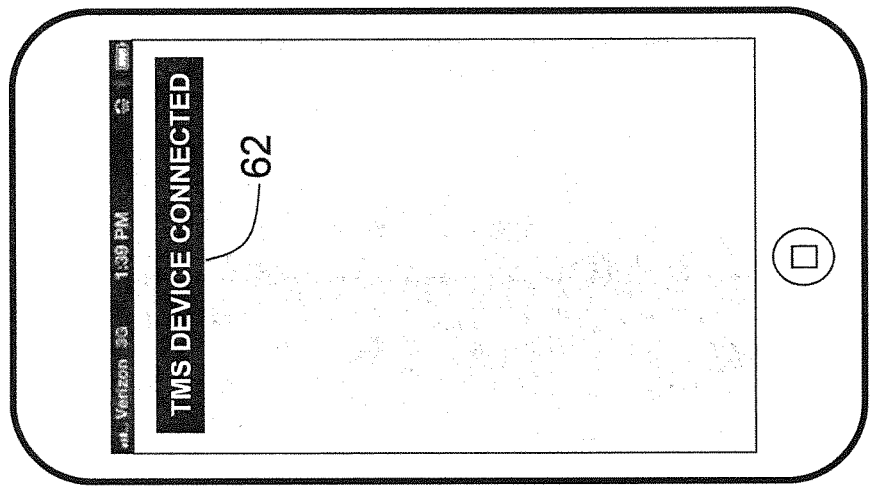
FIG. 7B shows the wording that would come up on the smart phone after it has successfully completed a wireless connection to the TMS device.

Once the APP 61 is touched, it will do everything needed to download the doctor's prescription into the TMS device 10 and upload patient use and device diagnostic information from the TMS device 10 to the central server 90. In this example, the first thing the APP 61 does is to confirm that the Bluetooth connection between the smartphone 60 and the TMS device 10 is active. When that connection is made, the smartphone 60 would display the "TMS DEVICE CONNECTED" 62 notification as shown in FIG. 7B. Next the smartphone 60 will indicate connection to the central server 90 by means of the Internet. This can be done using cellular data connections or through local Wi-Fi connection. All modern smartphones 60, tablets 70 or personal computers 75 have such a cellular data or Wi-Fi connection capability. The connection will involve a login process that will use patient and device information stored on the SIM card 45.

Once connected, the "SERVER CONNECTED" 63 message will appear on the smartphone 60 as shown in FIG. 7C. The scrollbar 64A and "UPLOADING TO SERVER" 65A message will then immediately appear. The scrollbar 64A will display the progress of the upload of patient use and device diagnostic data by motion to the right as is typical for many computer programs and APPs. When the scrollbar 64B is completely filled, the message "LOAD COMPLETE" 65B will be displayed as shown in FIG. 7D.

Figure 7A:
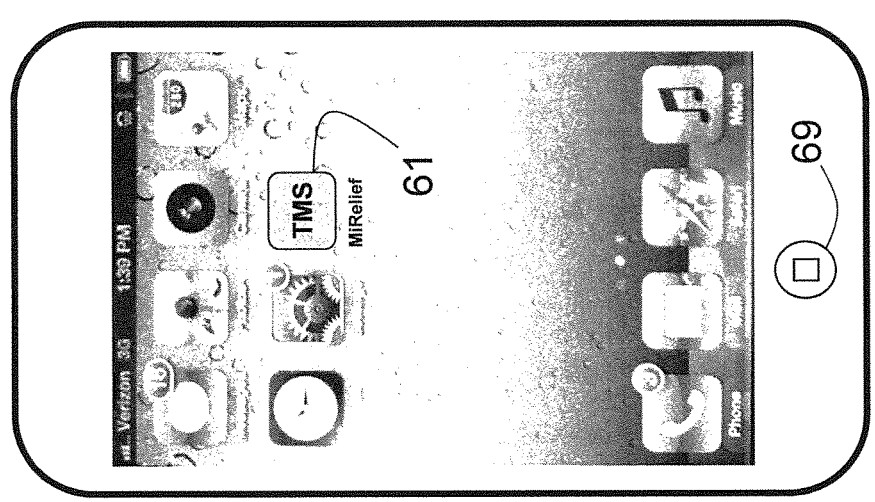
FIG. 7A is a front view of a smartphone showing several APPs including the TMS MiRelief APP.

The next and last step would then begin with the message "CHECKING FOR NEW PRESCRIPTIONS" 66A shown in FIG. 7D. The APP 61 would then securely download the new prescription information to the TMS device 10 through the Bluetooth connection where the information would be stored on the SIM card 45. Upon completion of these actions, the message "CHECKING FOR NEW PRESCRIPTIONS" 66A would disappear and the message "PRESCRIPTION DOWNLOAD SUCCESSFUL" 66B would appear as shown in FIG. 7E. At this point pressing the main button 69 would return the smartphone 60 to the configuration and screen display as shown in FIG. 7A.

Of course it is envisioned that while the description above has every part of the process being successfully completed, there would be appropriate error messages and help screens in the case of there being a problem. Such messages could include "TMS DEVICE NOT FOUND" with instructions to make sure it is close enough and turned on and that the Bluetooth connection has been previously made. Ideally, the initial Bluetooth connection is made with help by a nurse in the doctor's office. Similarly a message "SERVER NOT FOUND" followed by information telling the patient why, would be a possible presentation. Such reasons could include the messages "WIFI DATA DISABLED," "CELLULAR DATA DISABLED" where the patient needs to go to their settings to allow Internet data connectivity. Other reasons could be "NO WIFI AVAILABLE" or "NO CELLULAR DATA AVAILABLE". In addition, if the prescription is not available, instead of message 66B, the smartphone 60 would display "PRESCRIPTION NOT AVAILABLE, CHECK WITH YOUR DOCTOR".

An APP on a tablet 70 or a program that runs on a personal computer 75 would do essentially the same thing as the APP 61 disclosed for use with the smartphone 60 as shown in FIGS. 7A-7E inclusive.

While we have described the process for data communication between the TMS device 10 and the central server 90 as initiated by an APP 61 on a smartphone 60, it is also envisioned that the APP/program could reside on the TMS device 10 itself. In one example, it would be on the SIM card 45, itself. If the APP/program is on the TMS device 10 then once the Bluetooth connection is established, the APP/program could run automatically on the computational device 55. Such "Autorun" capability is well known.

It is also envisioned that if the TMS device 10 connects directly to the central server 90 through WiFi, a phone line with a modem wired Ethernet connection or a cellular data connection, that the TMS device 10 would initiate the process described above for downloading and uploading. If the TMS device 10 has an alphanumeric display it could also display the status messages described above for use on a smartphone.

FIG. 8 shows a schematic view of an adapter 100, which provides an alternative means to communicate information between the central server 90 of FIG. 6 and the TMS device 10. In this case, the SIM card 45 would be removed from the TMS device 10 and inserted into the slot 102 in the adapter 100. The USB plug (male) connector 104 of the adapter 100 can then be inserted into a USB receptacle (female) connector in a personal computer 75. If the SIM card 45 or adapter 100 has autorun software on it, then the process for connecting to the central server 90, uploading data from the SIM card 45 and downloading new programs would proceed much as it does as shown in FIGS. 7A-7E. If autorun is not used, then the patient would start a program on their personal computer 75 which would do the same thing.

The adapter 100 is also designed to work with smartphones 60 or tablets 70 that may not have a USB connector. The female mini-USB connector 106 allows the adapter 100 to be connected through a cable (not shown) to a smartphone 60 or tablet 70. For example the cable could have a male mini-USB connector on one end to connect to the mini-USB receptacle 106 and an iPhone male connector on the other. Once connected to a smartphone 60 or tablet 70 an APP 61 as shown in FIGS. 7A-7E could be used to communicate between the SIM card 45 and server 90 or, as described above for the personal computer autorun process, the APP 61 function could reside on the SIM card 45 or in memory on the adapter 100 which would then run automatically on the smartphone 60 or tablet 70 when connected.

It is also envisioned that instead of the mini-USB receptacle (female) connector 106, a standard or micro-USB connector or other type of connection socket could be used. Finally, the adapter 100 might not have the receptacle 106 but come with cables with USB receptacle connectors that would allow one to connect the USB plug connector 104 to smartphones 60 or tablets 70.

Figure 9:
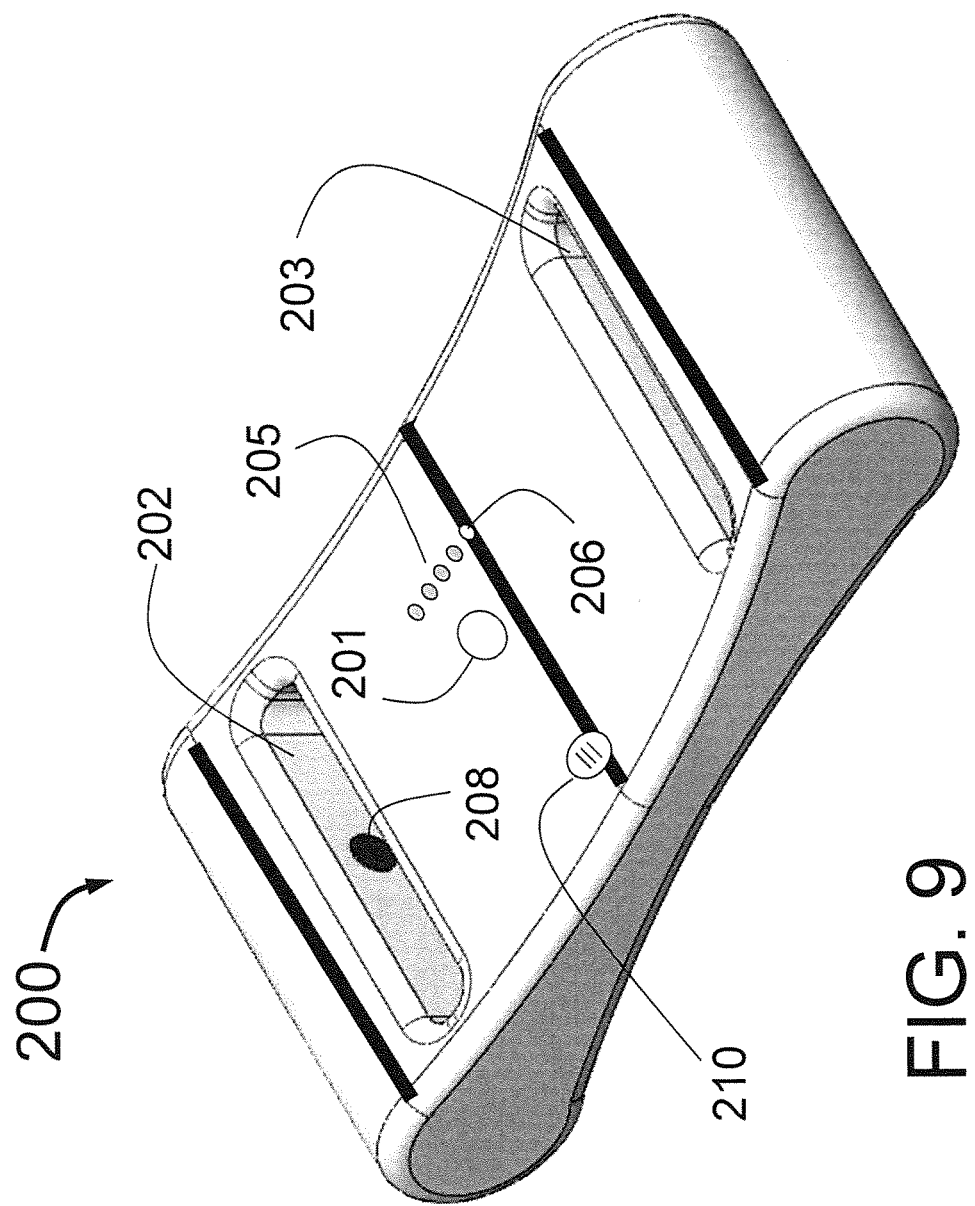
FIG. 9 illustrates an embodiment of the present invention TMS device showing the top of the device including finger slots with finger sensors designed to detect the presence of fingers within the finger slots.

FIG. 9 illustrates an embodiment of the present invention TMS device 200 showing the top of the device including finger slots 202 and 203 with finger sensor 208 shown in slot 202. A power or start button 201 activates the TMS device 200 and the initiates a charge and treat cycle. LEDs 205 light sequentially to show the progress of the charging of the capacitors and LED 206 lights when the charge is complete ideally green. A audio transducer which could be a small loudspeaker or piezo electric transducer provides sounds designed to provide status and guide the use of the TMS device 200. The audio transducer can provide sounds ticks, beeps, tones or recorded or synthetic speech for any or all of the following events:
  1. Power is on
  2. Capacitors are charging
  3. Charge is completed
  4. Count down to pulse delivery
  5. Pulse is delivered
  6. Error in use
  7. Fingers need to be inserted into the slots
  8. Device needs to be placed against the head Ideally the TMS device 200 method of use would be as follows:
1. Use the start button 201 to initiate charging of the TMS device 200 capacitors.
2. The charging LEDs 205 will show the progress of the charging.
3. The LED 206 will light and a sound from the audio transducer 210 will indicate the capacitors are fully charged and the TMS device 200 is ready to deliver a pulse.
4. The patient would then pick up the TMS device and place it in the appropriate location with the patient's fingers in the slots 202 and 203.
5. The finger sensor 208 in slot 202 when activated by the patient's fingers or thumb will initiate a short count down with associated sounds played through the audio transducer 210. An optional light or display or the LED 206 could also blink providing a visual indication of the count down. Ideally, such a count down would be a sequence of accelerating ticks played through the audio transducer 210 ending with the delivery of the pulse and an additional sound played through the audio transducer 210.

6. The sequence 1-5 can be repeated for each pulse delivered or a preset number of pulses can be delivered one after the other if the TMS device is so programmed.

7. If the patient's fingers are not placed into the slots after a first time out period, the TMS device 200 will alert the patient. Such an alert can be the flashing of one or more of the LEDs and/or a sound or spoken message played through the audio transducer. The patient then alerted would place fingers in the slots 202 and 203 to start the countdown, then move the TMS device 200 to its appropriate delivery location.

8. If the patient still fails to properly use the TMS device 200 within a second preset period, then the device will notify the patient with a sequence of LEDs 205 and/or 206 on and off and/or play a sound or spoken message through the audio transducer 210. All LEDs will then turn off and the capacitors will be discharged internally. Steps 1-5 would then need to be followed to restart delivering pulses.

A second finger sensor (not shown) could be in slot 203 and the activation of the count down could require both finger sensors be activated or as described above—only one.

It is also envisioned that a thumb sensor in a separate slot or on the outer surface of the TMS device 200 could be used instead of the finger sensor 208 and or its mate in the slot 203.

FIG. 10 illustrates an embodiment of the present invention TMS device 300 showing the bottom of the device including finger sensor 308 and head sensor 309. The top of the TMS device can include LEDs, power button, and audio transducer shown for the TMS device 200 of FIG. 9. The advantage of the added head sensor 309 is that while the count down could begin with the patient placing fingers in the slots 302 and 303 perhaps as a steady ticking sound, the TMS device 300 would wait until the head sensor 309 is activated to begin the acceleration of the ticking sounds and then deliver the pulse. If the head sensor is not activated within a head sensor first time interval, then an alert as disclosed in step 7 or the method above could be activated. If after a head sensor second time interval, still no activation of the head sensor 309, then the actions in step 8 above shutting down the TMS device 300 would occur.

It is envisioned that the time for the count down could be programmable or adjusted with a switch or dial. It is also envisioned that the head sensor could be used without the finger sensor(s). In such a case, the count down could begin automatically when the capacitors are charged and accelerate upon activation of the head sensor.

For the purpose of this application, body sensors 320 include head sensors 309 and finger sensors 308 as well as any other mechanical, optical, heat, pressure, infra-red or capacitive sensor that is used to sense proper use or positioning of the TMS device 300. As such these body sensors 320 each have two states an activated state when the a portion of the patient's body including but not limited to the patient's fingers, thumbs, neck, face or head is sensed and an unactivated state when it is not sensed. If an optical sensor is used then it can be a two piece sensor with a light source and a light detector where blocking the light from the source will cause activation. The optical sensor can also be a photodetector which can sense a change in light without the need for a separate source. Such an optical sensor can be in the visible or infra-red range.

While the primary use of a TMS device is to deliver magnetic pulses into the brain of a human patient, it is also envisioned that a TMS device could be used to deliver magnetic pulses to non-invasively stimulate tissue in other portions of the body. For example, there may be therapeutic effects of delivery of a magnetic pulse to stimulate the Vagus nerve in the neck or nerves in the spinal chord.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A transcranial magnetic stimulation (TMS) device for delivery of magnetic pulses into the body of a patient including:

a TMS housing having a power switch to electrically activate said TMS device, said TMS device being adapted to be displaced by a user from a first position displaced from a patient's body to a second position adjacent to or contiguous to said patient's body defining a pre-set distance from said patient's body;

at least one capacitor within said TMS housing to store electrical energy;

at least one wire coil within said TMS housing for delivering a magnetic pulse when an electrical current from the at least one capacitor is caused to flow through the at least one wire coil;

a charging circuit within said TMS housing to charge the at least one capacitor;

at least one body sensor mounted within said TMS housing having an unactivated state and an activated state, said at least one body sensor for determining if said TMS housing is within said pre-set distance from said patient's body when said power switch activates said TMS device, whereby when said at least one body sensor is in its second position, then said at least one body sensor is in said activated state; and a control circuit connected to the at least one body sensor, the control circuit is adapted to initiate the delivery of the a magnetic pulse by causing an electrical current from the at least one capacitor to flow through the wire coil, the control circuit further having a countdown timer circuit which counts down for a preset time period, said control circuit initiating discharge of the at least one capacitor subsequent to the preset time period only if the at least one body sensor is in the activated state;

where the control circuit further counts down for the preset time period, and the control circuit is adapted to initiate the delivery of a magnetic pulse by discharging the at least one capacitor through the at least one wire coil after a countdown timer has completed counting for the preset time period, the countdown timer includes means to notify the patient that a countdown is in progress, the means to notify the patient that a countdown has begun utilizes a sequence of sounds, and the sequence of sounds accelerates with reduced time between sounds in the sequence during the preset time period prior to the pulse being delivered for notification to the patient that the TMS device is in the preset time period.

2. The TMS device of claim 1 where the preset period for the countdown timer circuit is programmable.

3. The TMS device of claim 1 where the preset period for the countdown timer is adjustable.

4. The TMS device of claim 1 where the sounds include a ticking sound.

5. The TMS device of claim 1 where the at least one body sensor is a head sensor.

6. The TMS device of claim 1 where the at least one body sensor is a finger sensor.

7. The TMS device of claim 4 wherein the TMS housing further includes at least one slot to facilitate placement of the patient's fingers during delivery of the magnetic pulse, where a finger sensor is located within a portion of the at least one slot.

8. The TMS device of claim 7 where there are two finger sensors, one for the fingers of each hand.

9. The TMS device of claim 8 where the at least one body sensor is in the activated state only if both finger sensors are in an activated state.

10. The TMS device of claim 1 where the at least one body sensor is a mechanical switch activated by pressure.

11. The TMS device of claim 1 where the at least one body sensor is an optical sensor.

12. The TMS device of claim 1 where the at least one body sensor is a capacitive sensor.

13. The TMS device of 1 where the control circuit further includes a full charge patient notification selected from the group of a visual patient notification, an audible patient notification, or a vibratory patient notification.

14. A transcranial magnetic stimulation (TMS) device for delivery of magnetic pulses into the body of a human patient including:
   at least one capacitor to store electrical energy;
   at least one wire coil for delivering a magnetic pulse when an electrical current from the at least one capacitor is caused to flow through the at least one wire coil;
   a charging circuit to charge the at least one capacitor;
   at least one body sensor having an unactivated state and an activated state, the activated state defining that the TMS device has been displaced from a first positional location to a second positional location sufficiently close to the body of the patient to permit delivery of the magnetic pulse; and
   a control circuit connected to the at least one body sensor, the control circuit adapted to initiate the delivery of a magnetic pulse when the control circuit causes the electrical current from the at least one capacitor to flow through the at least one wire coil, the control circuit further including a countdown timer that will count for a preset time period, the control circuit further having a notification mechanism to provide a patient notification, the at least one body sensor activated state initiating a function of the control circuit selected from the group of starting the countdown timer; initiating the delivery of the magnetic pulse, and initiating the patient notification,
   where the countdown timer includes means to notify the patient that a countdown is in progress, the means to notify the patient that a countdown has begun utilizes a sequence of sounds, and the sequence of sounds accelerates with reduced time between sounds in the sequence during the preset time period prior to the pulse being delivered for notification to the patient that the TMS device is in the preset time period.

15. The TMS device of claim 14 where failure of the at least one body sensor to achieve said activated state within a preset time after the countdown timer begins will initiate a function of the control circuit selected from the group of restarting a countdown timer circuit, initiating the patient notification, and turning off the TMS device.

16. The TMS device of claim 14 where the preset period for the countdown timer is programmable.

17. The TMS device of claim 14 where the at least one body sensor is a head sensor.

18. The TMS device of claim 14 where the at least one body sensor is a finger sensor.

19. The TMS device of claim 14 where the at least one body sensor is a mechanical switch activated by pressure.

20. The TMS device of claim 14 where the at least one body sensor is an optical sensor.

21. The TMS device of claim 14 where the at least one body sensor is a capacitive sensor.

22. The TMS device of claim 1 where the control circuit further includes a full charge patient notification selected from the group including:
   a. a visual patient notification,
   b. an audible patient notification, or
   c. a vibratory patient notification.

23. A transcranial magnetic stimulation (TMS) device for delivery of magnetic pulses into the body of a human patient including:
   at least one capacitor to store electrical energy;
   at least one wire coil for delivering a magnetic pulse when an electrical current from the at least one capacitor is caused to flow through the at least one wire coil;
   a charging circuit to charge the at least one capacitor;
   at least one body sensor having an unactivated state and an activated state, the activated state defining that the TMS device has been displaced from a first positional location to a second positional location sufficiently close to the body of the patient to permit delivery of the magnetic pulse; and
   a control circuit connected to the at least one body sensor, the control circuit adapted to initiate the delivery of a magnetic pulse when the control circuit causes the electrical current from the at least one capacitor to flow through the at least one wire coil, the control circuit further including a countdown timer that will count for a preset time period, the control circuit further having a notification mechanism to provide a patient notification, the at least one body sensor activated state initiating a function of the control circuit selected from the group of starting the countdown timer; initiating the delivery of the magnetic pulse, and initiating the patient notification;
   where the countdown timer includes means to notify the patient that a countdown is in progress, and the means to notify the patient that a countdown has begun utilizes a sequence of sounds, the sounds include a ticking sound.

24. The TMS device of claim 23 where failure of the at least one body sensor to achieve said activated state within a preset time after the countdown timer begins will initiate a function of the control circuit selected from the group of restarting a countdown timer circuit, initiating the patient notification, and turning off the TMS device.

25. The TMS device of claim 23 where the preset period for the countdown timer is programmable.

26. The TMS device of claim 23 where the at least one body sensor is a head sensor.

27. The TMS device of claim 23 where the at least one body sensor is a finger sensor.

28. The TMS device of claim 23 where the at least one body sensor is a mechanical switch activated by pressure.

29. The TMS device of claim 23 where the at least one body sensor is an optical sensor.

30. The TMS device of claim 23 where the at least one body sensor is a capacitive sensor.

* * * * *